US010299706B2

(12) United States Patent
Pasichnyk et al.

(10) Patent No.: US 10,299,706 B2
(45) Date of Patent: May 28, 2019

(54) METHOD OF NONINVASIVE MEASUREMENT OF BLOOD GLUCOSE CONCENTRATIONS AND APPARATUS FOR THE IMPLEMENTATION THEREOF

(71) Applicant: Mark Bosin, Kharkov (UA)

(72) Inventors: Leonid Pasichnyk, Kharkov (UA); Mark Bosin, Kharkov (UA)

( * ) Notice: Subject to any disclaimer, the term of this patent is extended or adjusted under 35 U.S.C. 154(b) by 498 days.

(21) Appl. No.: 15/182,924

(22) Filed: Jun. 15, 2016

(65) Prior Publication Data

US 2016/0367175 A1 Dec. 22, 2016

Related U.S. Application Data

(60) Provisional application No. 62/180,088, filed on Jun. 16, 2015.

(51) Int. Cl.
*A61B 5/00* (2006.01)
*A61B 5/145* (2006.01)
(Continued)

(52) U.S. Cl.
CPC ...... *A61B 5/14532* (2013.01); *A61B 5/14558* (2013.01); *A61B 5/1495* (2013.01);
(Continued)

(58) Field of Classification Search
CPC ............ A61B 5/14532; A61B 5/14558; A61B 5/6826; A61B 2562/0238; A61B 5/1495; A61B 5/6844; A61B 5/6816
See application file for complete search history.

(56) References Cited

U.S. PATENT DOCUMENTS 5,383,452 A 1/1995 Buchert
5,788,632 A 8/1998 Pezzaniti et al.
(Continued)

FOREIGN PATENT DOCUMENTS

KR 10-0587742 6/2006

OTHER PUBLICATIONS

Bazaev N.A., Masloboev J.P., Selishchev S.V. Optical Methods of Noninvasive Determination of Blood Glucose Levels. Medical Facilities 2011, No. 6 (270) S.29-33.
(Continued)

*Primary Examiner* — Eric F Winakur
*Assistant Examiner* — Abid A Mustansir

(57) ABSTRACT

A method and apparatus for non-invasive blood glucose measurement are disclosed. The methods and apparatus utilize exposing a biological object supplied with blood and capable of transmitting infrared radiation therethrough, to an incident beam of polarized infrared radiation with a given angular position of a polarization plane, determining an angular position of a polarization plane of the radiation transmitted through the biological object with a polarizer-analyzer, and measuring an angle shift between said angular positions of the polarization planes of the incident and transmitted radiation, and calculating a glucose concentration C. The methods and apparatus further utilize measuring the length and oscillations of a whisker connected to the polarizer-analyzer and to a rigid support so as to calculate the instantaneous positions of the polarizer-analyzer.

16 Claims, 1 Drawing Sheet

(51) Int. Cl.
*A61B 5/1455* (2006.01)
*A61B 5/1495* (2006.01)

(52) U.S. Cl.
CPC .......... *A61B 5/6816* (2013.01); *A61B 5/6826* (2013.01); *A61B 5/6844* (2013.01); *A61B 2562/0238* (2013.01)

(56) References Cited

U.S. PATENT DOCUMENTS

| | | | |
|---|---|---|---|
| 6,804,002 | B2 | 10/2004 | Fine et al. |
| 8,743,355 | B2 | 6/2014 | Korman |
| 9,295,419 | B2 | 3/2016 | Weiss et al. |
| 2014/0036254 | A1* | 2/2014 | Bosin ................ A61B 5/14532 356/51 |
| 2014/0330097 | A1* | 11/2014 | Weiss ................... A61B 5/1455 600/316 |

OTHER PUBLICATIONS

Joslin's Diabetes Mellitus. 14th edition. Eddited by C.R.Kahn, G.C.Weir, G.L.King, A.M.Jacobson, A.C.Moses, R.J. Smith. Lippincott Williams & Wilkins ISBN: 0-7817-2796-0.

Normal Glucose Homeostasis. Chapter 2 in Principles of Diabetes Mellitus. Muhammad Z. Shrayyef and John E. Gerich. Poretsky L. (Ed.) 2010, XVI, 852 p. ISBN: 978-0-387-09840-1.

John L. Smith. The Pursuit of Noninvasive Glucose: "Hunting the Deceitful Turkey", 2nd Ed. (2011), pp. 35-42, 45-46, 49.

A.Gustafsson, F.Reinhardt, G.Biasiol and E.Kapon. Low pressure organometallic chemical vapor deposition of quantum wires on V-grooved substates // Applied Physics Letters, 1995, V.67, p. 3673.

J.Maire, M.Nomura. Reduced Thermal Condactivities of Si 1D periodic structure and Nanowires // Jpn.J.of Appl Phys, 2014, V.53—C.06JE09.

* cited by examiner

METHOD OF NONINVASIVE MEASUREMENT OF BLOOD GLUCOSE CONCENTRATIONS AND APPARATUS FOR THE IMPLEMENTATION THEREOF

CROSS-REFERENCE TO RELATED APPLICATIONS

This application claims priority to U.S. Provisional Application 62/180,088, filed Jun. 16, 2015 and entitled NON-INVASIVE MEASUREMENT OF GLUCOSE LEVEL IN HUMAN BLOOD, the entire contents of which are hereby incorporated by reference.

FIELD OF THE INVENTION

The present teachings relate in general to the non-invasive measurement of blood glucose concentration in human blood, and to an apparatus for conducting such measurements, which provides comfort and safety advantages to patients suffering from diabetes.

BACKGROUND

The possibility of a non-invasive diagnosis of blood glucose levels became a subject of researchers' interest over 30 years ago. Since then, there have been more than a dozen different methods of the measure thereof, based on fundamentally different effects. However, optical methods for determining concentration of glucose in blood were and remain the most attractive ones. The main advantage of such methods is primarily human safety. Numerous experiments confirm the possibility of development of a non-invasive blood glucose meter (NG) based on optical methods (Bazaev N. A., Masloboev J. P., Selishchev S. V. *Optical Methods of Noninvasive Determination of Blood Glucose Levels*. Medical Facilities 2011, No 6 (270) S.29-33). The reasons that prior attempts at developing NG did not succeed lie in the peculiarities of the physiology of each individual, the difficulties of interpreting the results obtained, the need for selection of optimal instrument calibration and so on.

During development of NG in the 1980s and 1990s there were high hopes for spectrophotometric methods. The visible part of the spectrum is not suitable for these measurements since glucose is substantially transparent, that is, glucose has weak light absorption. Therefore, efforts have been directed at creating a spectrophotometric NG in the infrared spectral region. The main obstacle in this field is the presence of a large amount of water in biological tissue, which strongly absorbs infrared light. Nevertheless, there are three "transparency windows" in the following wavelength ranges: 1) below 1.35 µm; 2) 1.55-1.85 µm; and 3) 2.1-2.3 µm. In the second and third ranges, there are absorption peaks specific to glucose, which were used to determine the concentration of glucose in the blood. Multi-wavelength spectrophotometry techniques were used in such determinations. It was possible to obtain and measure small concentrations of glucose with the help of calibrated solutions of glucose and background materials. However, when used for actual biological objects—for example human fingers—difficulties arose, and so the developers failed to bring the described methodology to the prototype level.

For this reason, over the last decade, many attempts have been made to measure glucose concentrations in human blood by polarimetry. Polarimetry is used for the quantitative analysis of solutions with optically active substances, such as glucose. Such materials rotate the plane of polarization of a polarized beam transmitted therethrough by the angle of $\alpha = \alpha_{sp} * l * c$, where $\alpha$, $\alpha_{sp}$ are the angle of the polarization plane rotation and its specific value; c is the concentration of glucose, and l is the optical path length. The specific value of the angle of the polarization plane rotation for glucose is $+56.2°[1/(g/dL)*dm]$.

Given that the average length of the optical path of blood vessels in the human finger is on the order of about 1 mm, the change in glucose concentration at 1 mg/dL will produce rotation of the polarization plane of only about 0.000562°, that is, a little over 2 seconds of arc. Determination of such angles by measuring the change in the intensity of the light beam when the analyzer is rotated at such angles is extremely difficult, and remains unsolved in the art. This is due to three factors. First, the intensity change due to rotation of the polarization plane for so little angle is extremely low. Second, the intensity of the light beam passing through a "polarizer-finger-analyzer (second polarizer)" arrangement is affected not only by the polarization plane rotation in a finger, which is related to the concentration of glucose in the blood, but also by numerous physical and biological processes occurring in the finger, which are impossible to take into account. Third, it is very difficult to accurately measure the rotation of a mechanical part by an angle of a few arc seconds. These three factors, in fact, are the obstacles that still have not been overcome.

SUMMARY

According to one exemplary embodiment, there is disclosed a method for the non-invasive measurement of blood glucose concentration in human blood, based on an accurate measurement of the angle shift of the polarization plane of radiation transmitted through a biological object such as a human body organ (e.g. the earlobe or the digital pulp of the terminal phalanx of a finger of the hand), by excluding the effect of physical and biological processes in the human body organ on the result, i.e. by measuring just the mechanical angle of the rotation.

In another exemplary embodiment, there is disclosed a method of accurate measurement of said angle shift via measurement of a linear value, connected with said angle shift.

In another exemplary embodiment, a new physical means for accurate measuring said linear value is disclosed.

In a further exemplary embodiment, there is disclosed an apparatus for non-invasive measurement of blood glucose concentration in human blood based on the method disclosed herein.

In yet another exemplary embodiment, there is disclosed a method for individual calibration of the function of the angle shift of the polarization plane vs. a glucose concentration simultaneously measured by an absolute invasive method.

In yet another exemplary embodiment, there is disclosed a method of determining the angle of rotation of the polarization plane or the angle of rotation of a polarizer by utilizing a whisker disposed between two poles of a permanent magnet and connected to a point on the polarizer and to a rigid support.

BRIEF DESCRIPTION OF THE FIGURES

Advantages of embodiments of the present invention will be apparent from the following detailed description of the exemplary embodiments. The following detailed description should be considered in conjunction with the accompanying figures in which.

DETAILED DESCRIPTION

Figure 1:
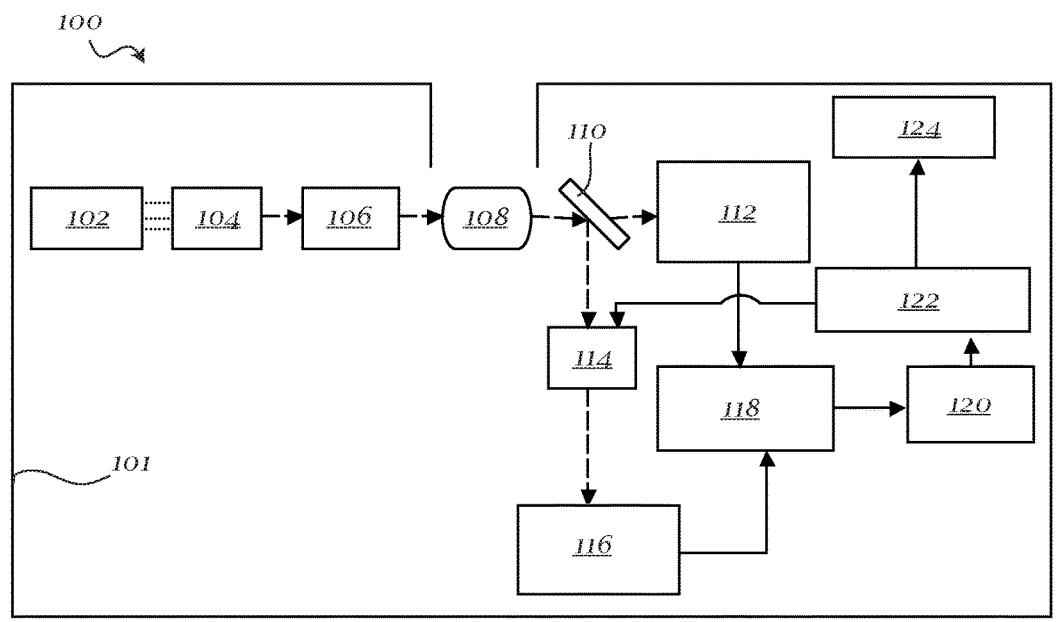
FIG. 1 illustrates a schematic diagram of an exemplary embodiment of an apparatus for non-invasive glucose measurement, according to the present teachings.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiment are not necessarily to be construed as preferred or advantageous over other embodiments. Moreover, the terms "embodiments of the invention", "embodiments" or "invention" do not require that all embodiments of the invention include the discussed feature, advantage or mode of operation.

Polarimetry is used for quantitative analysis of solutions with optically active substances. Such substances deflect the optical vector $\vec{E}$ of radiation transmitted therethrough (i.e., turn the polarization plane) by a certain characteristic angle $$\alpha = \alpha_{sp} \cdot c \cdot l \qquad (1)$$

where $\alpha$ is the angle of rotation (or angle shift) of the polarization plane (i.e., the rotation of vector $\vec{E}$); $\alpha_{sp}$ is the specific value of the angle of rotation of the polarization plane (for glucose, $\alpha_{sp}=56.2°$ 1/[(g/dl)·dm]); l is the optical path length; and c is the concentration of glucose. Equation (1) is valid only for optically homogeneous media, i.e., when the concentration of the optically active substance does not change throughout the entire optical path length. Otherwise, Equation (1) should be written in differential form:

$$d\alpha = \alpha_{sp} \cdot c \cdot dl \qquad (2)$$

Then, the resulting angle of rotation of the polarization plane will be equal to $$\alpha = \alpha_{sp} \cdot \int_L c \cdot dl \qquad (3)$$

In case of an inhomogeneous medium having a length L, c=c(l), i.e.

$$\alpha = \alpha_{sp} \cdot \int_L c(l) \cdot dl \qquad (3a)$$

At any function c(l), Equation (3a) does not result in a linear dependence of $\alpha(l)$. A biological object (e.g., earlobe, phalanx, etc.) can be a homogeneous medium (c=const), if a person does not suffer from diabetes because glucose moves freely from the blood into the extracellular fluid and then into cells. In patients with diabetes, there exist obstacles to the spread of blood glucose into the extracellular fluid, and therefore the biological object is an inhomogeneous medium. In such cases, Equation (3a) is applicable, rather than Equation (1), as it was a priori expected in published attempts to create a polarimetric type non-invasive blood glucose meter.

Let us transform Equation (3a):

$$\alpha = \alpha_{sp} \cdot L \cdot \frac{1}{L} \int_L c(l) \cdot dl \qquad (4)$$

Here, $$\frac{1}{L} \int_L c(l) \cdot dl = \bar{c}_L \qquad (5)$$

is an average concentration of glucose $\bar{c}_L$ on the radiation beam path L. From Equations (4, 5), one can obtain:

$$\alpha = \alpha_{sp} \cdot \bar{c}_L \cdot L \qquad (6)$$

or $$\bar{c}_L = \frac{\alpha}{\alpha_{sp} \cdot L} \qquad (6a)$$

Equation (6a) gives us an average glucose concentration $\bar{c}_L$ on the optical path length L, which, in the case of an inhomogeneous medium, can differ greatly from the average glucose concentration in the liquid volume of, for example, an earlobe or a finger. The linear mean, in general, is connected with the volume mean by an equation to be determined, on the condition of the lack of change of the nature of the inhomogeneity of glucose distribution throughout the volume of the biological object, as well as of the position of the linear path of the radiation beam with respect to the biological object. The nature of the inhomogeneity of glucose distribution is defined solely by the patient's stage of disease, which may not change over the years. The position of the trajectory of the radiation beam in the biological object (for example, a finger), upon precise placement of the biological object on the object stage of the glucose concentration meter (which has to be guaranteed by the design of the instrument) depends on the individual parameters of the biological object, i.e., of the particular patient.

Thus, the distribution of glucose in a biological object, as well as the structural features of the biological object can only be defined for a particular patient. Accordingly, the specific formula linking the average linear glucose concentration $\bar{c}_L$ with a volume concentration $\bar{c}_V$ can be determined experimentally only for a particular patient. Therefore, an individual calibration is required.

Let the individual relationship between $\bar{c}_L$ and $\bar{c}_V$ be:

$$\bar{c}_L = \varphi(\bar{c}_V) \qquad (7)$$

Substituting (7) into (6a) gives the following equation:

$$\varphi(\overline{c}_V) = \frac{\alpha}{\alpha_{y\theta} \cdot L} \quad (8)$$

Resolving (8) with respect to $\overline{c}_V$ gives the following equation:

$$\overline{c}_V = \psi\left(\frac{\alpha}{\alpha_{y\theta} \cdot L}\right) \quad (9)$$

Let the function $\psi$ be expressed as a power series:

$$\overline{c}_V = a_0 + a_1\alpha + a_2\alpha^2 + \ldots + a_n\alpha^k \quad (10)$$

Our experiments have shown that in the case of healthy persons, just two terms may be left in the expansion (10):

$$\overline{c}_V = a_0 + a_1\alpha \quad (11)$$

In this case, using two points to determine the individual parameters $a_0$ and $a_1$ is sufficient for calibration. In the case of sick persons, the sought quantity $\overline{c}_V$ is equal to $$\overline{c}_V = \sum_{i=o}^{k} a_i \alpha^i \quad (12)$$

where the number of terms (k+1) is determined experimentally, while for the determination of the coefficients $a_1$, a (k+1) quantity of points, i.e., a (k+1) amount of punctures is necessary for measuring the glucose concentration by an accurate invasive method.

Thus, the volume concentration of glucose in a biological object is calculated using Equation (12) after the experimental determination of the angle of rotation of the polarization plane and the preliminary individual calibration (determination of i=0, 1, . . . , k;).

FIG. 1 shows a schematic diagram of an exemplary embodiment of an apparatus 100 for non-invasive glucose measurement, according to the present teachings. The source of infrared radiation can include a motionless housing 101, a polarized radiation beam source, for example a laser 102, which may be mounted in housing 101, an optical device 104, and a polarizer 106. A wide beam emitted by laser 102 passes through optical device 104, which transforms the wide beam to a narrow and slightly divergent beam with a transverse diameter of less than about 0.5 mm, for example, about 0.2-0.3 mm, a flat wave front, and divergence of no more than about one angular degree. The beam then passes through a first polarizer 106, from which a plane-polarized beam is emitted. The latter then passes through a biological object 108, for example a human body organ. The biological object may be mounted on an object stage 109 that is installed in the path of the plane-polarized beam and that is capable of precisely mounting the biological object thereon in a specific repeatable position. Examples of human body organs that may be used with these embodiments include, for example, an earlobe, the distal phalanx of a finger of the hand, or the digital pulp of the distal phalanx of a finger of the hand. For patient self-use of the apparatus, the earlobe may present a less comfortable object due to lack of easy visibility, and therefore in some exemplary embodiments, the object stage may be adapted to the finger, such that position of the finger is fixed, and such that the beam passes through the digital pulp of the distal phalanx of that finger.

In the biological object, due to the presence of glucose in human blood, the plane of polarization is rotated, as glucose is an optically active substance. A partial depolarization and scattering of the optical beam also takes place in the biological object. These phenomena cannot be taken into account mathematically, which is why a differential method of deducting all influences on the intensity of the beam (except the rotation of the polarization plane) is implemented in the exemplary embodiment of the apparatus. To this end, the beam transmitted through the biological object is divided by a splitter 110 into two beams, the first beam being sent directly to a first radiation receiver 112, while the second beam hits a second radiation receiver 116 after passing through a second polarizer 114 (the polarizer-analyzer). Splitter 110 may be capable of dividing the incident beam into two beams of equal intensities or, such that the maxima signals of the first 112 and second 114 radiation receivers are equal to each other.

Initially (prior to placing the biological object), the first and second polarizers 106 and 114 are established in parallel, i.e. the intensities of the rays that hit first and second receivers 112 and 116 are the same, and the output signals of the receivers 112, 116 are the same. After placement of the biological object, the beam intensities arriving at the receivers 112, 116 become diverse due to the rotation of the polarization plane in the biological object. The difference in the intensities of the beams depends exclusively on the polarization plane rotation in the biological object, which, in turn, depends on the concentration of glucose in the blood and the length of the optical path of the beam in the biological object.

The signals from the receivers 112, 116 enter an amplifier 118, and then these analog signals are converted into digital signals in analog-to-digital converter 120. The digital signals are then subtracted in a microcontroller 122. If the difference between the digital signals is not zero, a command is issued to an oscillating mechanism (not shown) for oscillating the second polarizer 114, which, upon receipt of the command, begins to perform angular oscillations at an angle $\pm\varphi$ about a position in which the difference between the intensities of the two beams is zero. This position clearly defines the angle of rotation of the polarization plane in the finger. Since the second polarizer approaches the "zero" position alternately from different angle sides, and the results are averaged, the presence of micro-plays or micro-slack in the mechanical system does not introduce additional errors. In addition, the amount of angular oscillations is set by the processor, so that by increasing the amount of such oscillations and calculating e.g. the statistical expected value we greatly reduce measurement error.

During the execution of the angular oscillations of the second polarizer 114, multiple measurements of the functions of the instantaneous values of the infrared radiation intensity transmitted through second polarizer 114 versus the instantaneous values of the angular positions of second polarizer 114 may be performed. In some exemplary embodiments, the extrema of these functions may be determined, and the angle shift may be calculated as a parameter of the distribution of these extrema. The parameter of extrema distributions of these functions may include a mode, a statistically expected value, and a distribution median. In further exemplary embodiments, the number of such measurements of these functions may exceed 100.

To determine the angle of rotation of the polarization plane in the biological object, or to determine the angle of rotation of the second polarizer 114 required for obtaining a zero difference between the intensities of the two beams formed after division by splitter 110, whiskers (also known as filamentary crystals or thread-like crystals) may be used. Whiskers are dislocation-free crystals. As dislocations are carriers of plastic deformation, and as whiskers are dislocation-free, it follows that the whole deformation of the whisker is elastic, i.e., the elasticity limit and the tensile strength are the same. Therefore, Hooke's law is applied throughout the whole deformation, i.e. mechanical stress unequivocally determines the extent of the whisker length.

Figure 2:
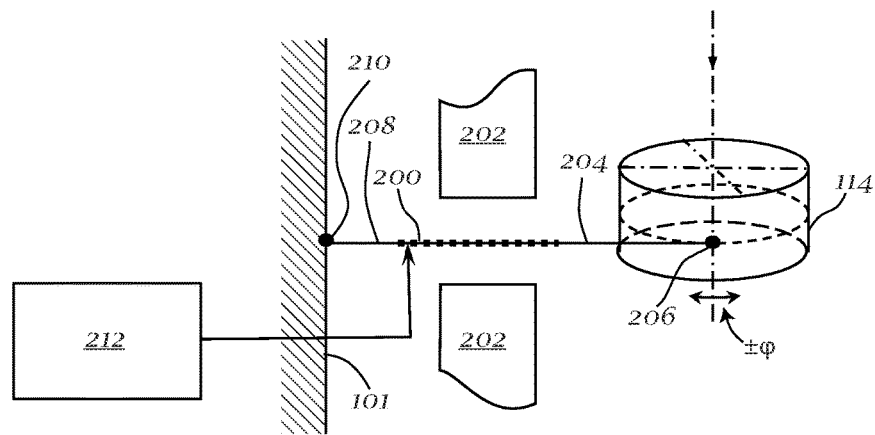
FIG. 2 illustrates a portion of an exemplary embodiment of the apparatus according to the present teachings, showing the layout of the whisker in relation to the second polarizer and the constant magnet.

FIG. 2 shows the layout of the whisker with respect to the second (rotatable) polarizer 114 and a permanent magnet 202. A first end of the whisker 200 is connected to a movable point 206 of the second polarizer 114 or of a cylinder (not shown) into which the polarizer-analyzer may be inserted. A second end of the whisker is connected to a fixed (immovable) support 210, for example motionless housing 101. "Connected" and "connecting" as used herein means attached or attaching directly or indirectly; for example, the first end of the whisker 200 may be connected to movable point 206 via a first rigid thread 204. Similarly, the second end of the whisker 200 may be connected to fixed support 210 via a second rigid thread 208.

The whisker is placed between the poles of a permanent magnet 202 such that the self-oscillation plane of whisker 200 is perpendicular to the magnetic force lines of magnet 202. Upon self-oscillations excited in the tensioned whisker 200 during the course of executing the above-described angular oscillations, a variable electromagnetic force is excited therein due to Faraday's law of electromagnetic induction. The frequency of electrical oscillations is measured with a high degree of accuracy by a frequency meter 212, which may be coupled to whisker 200. Thus, the oscillation frequency is easily converted into mechanical stress (whisker tension), which uniquely identifies the mechanical deformation (elongation or shortening of the whisker). The instantaneous values of the whisker length during the course of execution of the angular oscillations may be measured, and the instantaneous values of the angular position of second polarizer 114 corresponding to the instantaneous values of the length of whisker 200 may be calculated. Dividing the change in whisker length by the distance of the point 206 from the axis of the second polarizer rotation gives the value of its instantaneous angle.

Glucose concentration C in the human blood and the angle shift α of the polarization plane are strictly proportional by theory. However, our experiments show that, in the case where the optical beam passes through the digital pulp of the distal phalanx of a finger of the hand, this relationship differs from linear and may be presented in general by the equation $$C=f(\alpha). \tag{13}$$

The function $f$ depends on the optical beam path length in the finger, which, in turn, depends on the parameters of the capillaries present therein and, as shown by our experiments, the stage of the disease, which is particular to an individual. Therefore, individual calibration via a precise invasive technique is required. The resulting individual parameters are stored in the processor 122, and at a certain angle α calculations according to Equation 13 are made. The result is indicated on a display 124 in mmol/l or mg/dl.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A method for non-invasive measurement of glucose concentration in human blood, comprising:
    exposing a biological object supplied with blood and capable of transmitting infrared radiation therethrough, to an incident beam of polarized infrared radiation with a given angular position of a polarization plane;
    dividing the radiation transmitted through the biological object into a first part and a second part, the second part being directed to a polarizer-analyzer;
    determining an angular position of a polarization plane of the radiation transmitted through the biological object with the polarizer-analyzer;
    measuring an angle shift between said angular positions of the polarization planes of the incident and transmitted radiation; and
    calculating a glucose concentration C by the following formula:

$$C=f(\alpha),$$

where
    α is the angle shift, and
    $f$ is a function determinable for each individual by a calibration at several specific values of glucose concentration in blood measured by an absolute invasive method;
    wherein for determining said angular position of the polarization plane of the radiation transmitted through the biological object, the method further includes:
    executing angular oscillations of the polarizer-analyzer around an axis parallel to that of the incident beam;
    performing multiple measurements of the functions of a physical quantity dependent on instantaneous values of the infrared radiation intensity transmitted through the polarizer-analyzer versus instantaneous values of the angular positions of the polarizer-analyzer in the course of execution of said angular oscillations, said physical quantity being a difference between the intensity of said first part of the radiation and said intensity of the radiation transmitted through the polarizer-analyzer;
    determination of extrema of said functions; and
    calculation of said angle shift as a parameter of said extrema distribution.

2. The method of claim 1, wherein the number of said multiple measurements of said functions exceeds 100.

3. The method of claim 1, wherein the intensities of the first and second parts of the radiation are equal to each other.

4. The method of claim 1, wherein for determination of said instantaneous values of the angular position of the polarizer-analyzer the method further includes:
    providing a whisker;
    connecting a first end of the whisker to a stationary support;
    connecting a second end of the whisker to a point of the polarizer-analyzer, said point being movable in the course of executing said angular oscillations and so as to cause corresponding changes in the length of the whisker;

measuring the instantaneous values of the whisker length in the course of execution of said angular oscillations; and calculating the instantaneous values of the angular position of the polarizer-analyzer corresponding to the instantaneous values of the whisker length.

5. The method of claim 4, wherein the method further includes measuring the instantaneous values of the whisker self-oscillation frequency generated in the course of execution of said angular oscillations and calculating the instantaneous values of the whisker length.

6. The method of claim 5, wherein the method further includes:

providing a permanent magnet;

positioning the whisker between the poles of the permanent magnet such that the self-oscillation plane of the whisker is perpendicular to the magnetic force lines of the permanent magnet; and measuring instantaneous values of the self-oscillations of the whisker by measurement of the frequency of electric oscillations excited in the whisker.

7. The method of claim 1, wherein the biological object is a human body organ selected from the group consisting of an earlobe and a terminal phalanx of a finger of a hand.

8. The method of claim 1, wherein the wavelength of the infrared radiation lies in a wavelength range selected from the group consisting of: below 1.35 µm; 1.55-1.85 µm; and 2.1-2.3 µm.

9. The method of claim 1, wherein the parameter of said functions extrema distribution is selected from the group including a mode, a statistically expected value, a distribution median.

10. The method of claim 9, wherein the number of said multiple measurements of said functions exceeds 100.

11. An apparatus for non-invasive measurement of glucose concentration in human blood, comprising:

a polarized infrared radiation beam source;

an object stage installed on the path of said beam and capable of precisely mounting a biological object to be tested, in a specific repeatable position;

a polarizer-analyzer installed on the path of the radiation transmitted through the biological object;

a first radiation receiver capable of receiving radiation transmitted through the polarizer-analyzer and generating a first electric signal proportional to the intensity of radiation incident thereon;

a signal processing system, said first radiation receiver being connected to a first input of the signal processing system;

a control system;

a generator of mechanical angular oscillations of the polarizer-analyzer, around an axis parallel to that of the incident beam, said generator being adapted to be guided by the control system;

a means for measuring instantaneous values of the angular position of the polarizer-analyzer in the course of execution of said angular oscillations; and a whisker, a first end of the whisker being connected to a fixed support, and a second end of the whisker being connected to a point of the polarizer-analyzer, the point being movable in the course of executing said angular oscillations so as to cause corresponding changes in the length of the whisker.

12. The apparatus of claim 11, further comprising:

a second radiation receiver; and a beam splitter installed after the object stage and capable of dividing the incident beam into a first beam and a second beam, the first beam being directed toward the first radiation receiver and the second beam being directed toward the second radiation receiver so as to generate a second electric signal proportional to the intensity of radiation incident thereon, said second radiation receiver being connected to a second input of the signal processing system.

13. The apparatus of claim 12, wherein the splitter is capable of dividing the incident beam into two beams of equal intensities or so that the maxima of the first and second electric signals are equal to one another.

14. The apparatus of claim 11, further comprising a frequency meter and a constant magnet arranged so that the whisker is positioned between its poles and the whisker self-oscillation plane is perpendicular to magnetic lines of force, the whisker being coupled to the input of the frequency meter.

15. The apparatus of claim 11, wherein the polarized infrared radiation beam source comprises a laser and a polarizer.

16. The apparatus of claim 11, wherein the wavelength of the infrared radiation lies in a wavelength range selected from the group consisting of: below 1.35 µm; 1.55-1.85 µm; and 2.1-2.3 µm.

* * * * *